United States Patent [19]

Herrick

[11] Patent Number: Plant 7,299

[45] Date of Patent: Aug. 14, 1990

[54] *NEPHROLEPSIS EXALTATA* NAMED NAPA COTTAGE

[75] Inventor: Robert D. Herrick, St. Helena, Calif.

[73] Assignee: Cottage Gardens Nursery, St. Helena, Calif.

[21] Appl. No.: 368,048

[22] Filed: Jun. 9, 1989

[51] Int. Cl.[5] ..... A01H 9/00

[52] U.S. Cl. ..... Plt./89

[58] Field of Search ..... Plt./89

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new cultivar of *Nephrolepsis exaltata* named Napa Cottage, characterized by its rich green fronds and thick growth, compact and symmetrical growth habit which produces a full plant, excellent adaptability to grow strongly in relatively low and high light intensities, temperature tolerance, and its adaptability to various size pots without overgrowing.

1 Drawing Sheet

The present invention comprises a new and distinct cultivar of *Nephrolepsis exaltata,* known by the cultivar name Napa Cottage.

The new cultivar was discovered by the inventor Robert D. Herrick as a sport or mutation of an unnamed parent commonly known commercially as a Boston fern. The sport or mutation was discovered in the greenhouses of Cottage Gardens Nursery in Eureka, Calif. in July 1987, and was immediately recognizable due to its distinctive characteristics described below. The mutation was separated and a series of trials were conducted to make certain that the new cultivar was stable when asexually propagated, and to determine the suitability of various characteristics for commercial production, including its adaptability to temperature and light conditions, adaptability to large scale propagation, appearance, marketability, etc.

Initial asexual propagation by runners, and subsequent asexual propagation both by runners and by tissue culture, has clearly demonstrated that the combination of characteristics for Napa Cottage as described below are retained through successive generations of asexual reproduction.

Napa Cottage has not been observed under all possible environmental conditions. The phenotype may vary somewhat with variations in environment such as temperature, light intensity and daylength.

The following observations and measurements describe plants grown in St. Helena, Calif. under greenhouse conditions similar to those used in commercial practice. Both the description and color photograph are of a plant of Napa Cottage approximately 18 months old, except that the color values were obtained from a plant approximately 4 months old. However, the differences in color values between the respective ages is not significant, although some darkening with maturity will occur.

The following characteristics of Napa Cottage have been repeatedly observed and in combination distinguish Napa Cottage as a new and distinct cultivar:

1. The fronds are a rich green color, and together with a vigorous growth habit, provide thick growth and an overall lush green appearance.

2. Its compact size, symmetrical shape and great number of fronds produce a very full plant.

3. Napa cottage has shown excellent adaptability to grow well in high and low light intensities, making it an excellent cultivar for interior landscaping.

4. As with light, Napa Cottage has shown excellent tolerance to a wide range of temperatures. Although ideal growth temperatures are between 62°–80° F., Napa Cottage has been shown to tolerate temperatures as low as 50° F. and as high as 100° F., if the tolerance period is not prolonged.

5. The plants of Napa Cottage have shown excellent adaptability to very small to quite large pots, for use either as a hanging plant or a table fern. The plants do not tend to overgrow the container and maintain their lush green appearance in pots of various sizes.

The accompanying photographic drawing illustrates in top perspective view the new cultivar. The plant illustrated is 18 months in age, and the rich, full growth will be readily apparent. The photograph depicts color as accurately as possible with color illustrations of this type.

The color values described below were taken from a 4 month old plant in late May under combined natural and artificial light conditions. Color references are to The Royal Horticultural Society Colour Chart (R.H.S.). the values are believed to closely approximate the color illustrated in the photograph.

Botanical: *Nephrolepsis exaltata* cv Napa Cottage.

Origin: Mutation of unnamed cultivar.

Form: A mounded mass of fronds having aesthetically pleasing texture. Rich green, excellent for a small to medium-sized table fern. Thick, luxurious growth lends to its adaptability as a hanging plant.

Shape: Compact, symmetrical, with fronds radiating from the center of the plant and flowing out evenly over the sides of the pot.

Growth: Vigorous, upright to arching fronds that eventually hide the container. Full center crown, with vigorous, sturdy, young fronds that do not die back.

Foliage:

*Quantity.*—Numerous fronds, arising from the plant's central crown, and runners along the edge of the pot. Overall, a very "full" plant.

*Leaves.*—Orientation: Generally linear, with most of taper occurring near the frond tip. Size: Medium, with an average length of 35.6 cm (14.0″), and an average width (pinna tip to pinna tip when flattened) of 5.2 cm (2.1″). These dimensions depend on culture. The rachis is green with a prominent groove on the adaxial (upper) surface. Pubescence: Silvery-white hairs along entire length of rachis when young. Hairs become brown on older, mature fronds. Pubescence seems to disappear between pinna with maturity of the leaf, but there are conspicuous tufts of brown pubescence at bases of pinnae on mature fronds. Texture: Waxy feel to the fronds, giving the plant a hardy appearance. Gloss: Slight sheen, depending on culture.

*Leaflets.k*—Shape: Pinnae are simple, and have a noticeable arch. Arrangement: Primarily alternate, but sometimes opposite near the rachis base. Pinnae average 39 pairs (78 individual pinna) per leaf. Pinna on the outer ⅓ of the rachis are essentially planar, becoming less so closer to the base of the frond. At the base, noticeable pinnae twisting occurs, frequently such that the plane of the axis of the pinna may be greater than 90 degrees from a flat orientation. This gives the effect of increased fullness to the center of the plant. Individual mature pinnae are cupped upwards. Size: Typical length of mature pinnae (measured along the pinna midrib) is 25 mm (1.0″), with a width of 8 mm (0.3″), although some pinnae are larger than this. Margin: Undulate to crenate, especially near the pinna tip. Under magnification, small incisions are seen in the margin. No pubescence was observed to originate on the pinnae margin. Color: Upper side: Pinnae from base of leaf to approximately ⅔ of length of leaf, 137B. Under side: 137B. Upper side: 10–12 terminal pinnae of leaf, 137C-D adjacent rachis, 144B at tip. Under side: Slightly lighter. Upper side: Pinnae from ⅔ of leaf length to terminal 10–12 pinnae, 137C near rachis, 143C at top. Under side: Slightly lighter. Pinnae base: Oblique to truncate, with a slight clear to white pubescence visible under magnification. Pinna tip: Acute to obtuse. Midrib: Black, especially when viewed under magnification. The midrib conspicuously divides the pinna into two uneven components of approximately ⅓ and ⅔, with the larger portion always oriented towards the frond tip. Pinna shape: Oblong, sides generally parallel, with most taper occurring near the tip. Pinna scars: Circular to elliptic in outline, somewhat raised. There is a brown mark on the rachis at the base of each pinna. This coloration remains when pinna are removed.

*Buds.*—None. No spore have been noted on the cultivar. Asexual propagation is necessary to maintain the characteristics of the plant.

Other characteristics:

*Light intensity.*—Napa Cottage has the unique ability to adapt to various light intensities. Tests have shown that the plant will grow well in as low as 200 foot candles of light and as high as 4,000 foot candles. The ideal light intensity is between 1,200 and 2,500 foot candles for maximum growth rates. This adaptability makes it an ideal indoor plant where low light intensities prevail, particularly in commercial plantscapes. When the plant is exposed to long periods of low light intensities it shows no signs of deterioration as do many of the cultivars of the genus Nephrolepsis, thereby making it especially desirable to the trade.

*Nutrient feeding.*—In commercial greenhouse operations, feeding at a normal foliage feed that matches the soil mix the plant is planted in has proven to be most successful. On a constant feed basis, between 150 and 250 ppm nitrogen, 25 to 50 ppm phosphorus, and 100 to 200 ppm potasium appear to be ideal in a soilless mix. If bark or sawdust is present in the mix, adjustments must be made to account for the nitrogen lost to those components. In an indoor environment the plant requires very little feeding in order to maintain lush green growth.

*Temperature.*—Napa Cottage has a wide range of temperature tolerances. Ideal growth temperatures range between 62° F. and 80° F. However, it will tolerate temperatures between 50° F. and 100° F. without any ill effect, provided the exposure is not for prolonged periods of time. Other types of Nephrolepsis ferns will show signs of deterioration when exposed to the temperatures at either the high or low end of the above spectrum. This makes Napa Cottage especially adaptable to a wide range of uses in the home as well as commercial settings.

*Container adaptability.*—Because of the unique size and arrangement of fronds, Napa Cottage is well suited to a wide range of container sizes without overgrowing the pot. The narrow fronds and symmetrical shape make the plant suited to containers from 2¼″ to 10″ in diameter and larger. This feature makes it different from most Nephrolepsis, which tend to overgrow their containers and become woody looking and unattractive. The plant is uniquely suited for use as a hanging plant or a table fern.

General observations: Napa Cottage is unique when compared to other cultivars of *Nephrolepsis exaltata.* It is especially marketable and will be desirable to both the commercial plant industry and the end consumer. Its ease in growing, response to a variety of growing conditions, and its durability will appeal to the commercial producer. Its adaptability and rich lush green appearance, along with its unique shape and symmetry, will appeal to the retail florists, mass marketers, interiorscapers, and the homeowner.

I claim:

1. A new and distinct cultivar of *Nephrolepsis exaltata* named Napa Cottage, as illustrated and described.

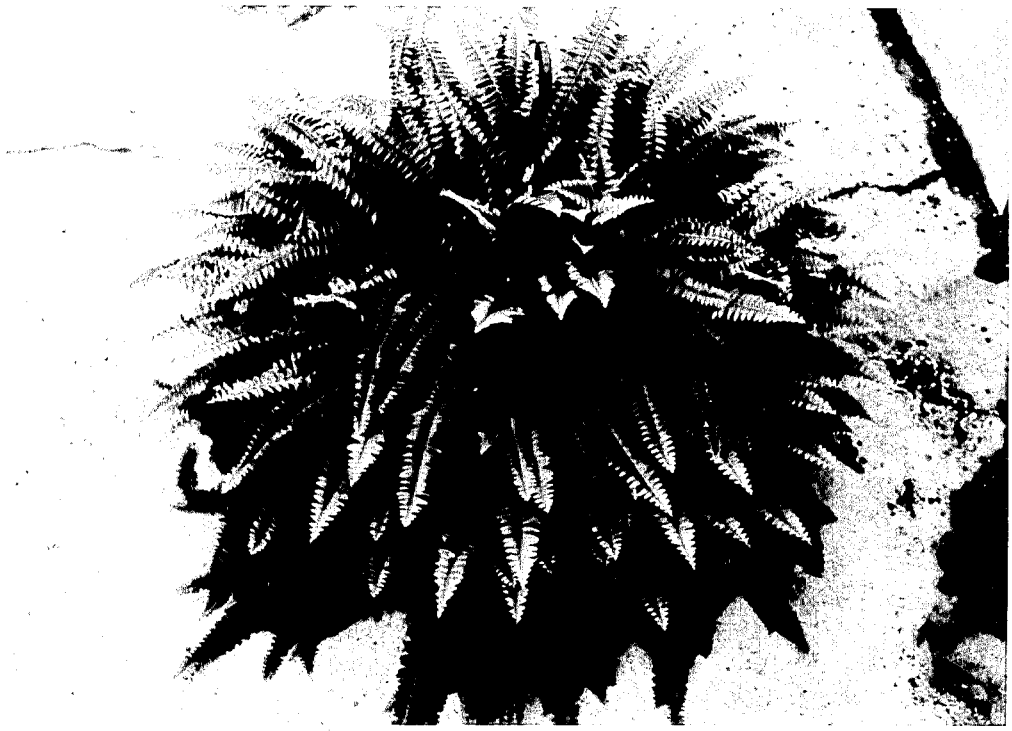

* * * * *